United States Patent
Li

(10) Patent No.: US 8,965,504 B2
(45) Date of Patent: Feb. 24, 2015

(54) SYSTEMS AND METHODS OF CHARACTERIZING MECHANICAL ACTIVATION PATTERNS FOR RHYTHM DISCRIMINATION AND THERAPY

(71) Applicant: Cardiac Pacemakers, Inc., St. Paul, MN (US)

(72) Inventor: Dan Li, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 38 days.

(21) Appl. No.: 13/781,178

(22) Filed: Feb. 28, 2013

(65) Prior Publication Data

US 2013/0231712 A1  Sep. 5, 2013

Related U.S. Application Data

(60) Provisional application No. 61/605,936, filed on Mar. 2, 2012.

(51) Int. Cl.
*A61N 1/362* (2006.01)
*A61N 1/365* (2006.01)

(52) U.S. Cl.
CPC .......... *A61N 1/3621* (2013.01); *A61N 1/36521* (2013.01); *A61N 1/36578* (2013.01)
USPC .................. 607/14; 607/18; 607/25; 607/119

(58) Field of Classification Search
USPC ......................................... 607/14, 18, 25, 119
See application file for complete search history.

(56) References Cited

U.S. PATENT DOCUMENTS

| 6,687,540 B2 | 2/2004 | Marcovecchio |
| 6,754,530 B2 | 6/2004 | Bakels et al. |
| 6,970,743 B2 | 11/2005 | Weinberg et al. |
| 7,010,347 B2 | 3/2006 | Schecter |
| 7,127,289 B2 | 10/2006 | Yu et al. |

(Continued)

FOREIGN PATENT DOCUMENTS

WO  WO-2011002535 A1  1/2011

OTHER PUBLICATIONS

Bank, Alan J, et al., "Echocardiographic Measurement of Mechanical Dyssynchrony in Heart Failure and Cardiac Resynchronization Therapy", US Cardiology, 2010;7(1):24-32, (2010), 9 pgs.

(Continued)

*Primary Examiner* — Catherine Voorhees
*Assistant Examiner* — Michael Carey
(74) *Attorney, Agent, or Firm* — Schwegman Lundberg & Woessner, P.A.

(57) ABSTRACT

An implantable sensor circuit can be configured to generate a first sensor signal representative of mechanical activation of a first chamber of a heart of a subject and a second sensor signal representative of mechanical activation of a second chamber of the heart. A chamber synchrony measurement circuit can be configured to generate a measure of synchrony of the mechanical activations of the first heart chamber and the second heart chamber using the first and second sensor signals, a tachyarrhythmia detector circuit, and a control circuit. The control circuit can be configured to receive an indication of a detected episode of tachyarrhythmia, and to initiate, select, or adjust a device-based therapy at least in part using the measure of synchrony of the mechanical activations in response to the tachyarrhythmia detection.

20 Claims, 8 Drawing Sheets

(56) References Cited

U.S. PATENT DOCUMENTS

| | | | |
|---|---|---|---|
| 7,206,634 | B2 | 4/2007 | Ding et al. |
| 7,209,786 | B2 | 4/2007 | Brockway et al. |
| 7,212,849 | B2 | 5/2007 | Zhang et al. |
| 7,274,961 | B1 | 9/2007 | Kroll et al. |
| 7,313,438 | B2 | 12/2007 | Zhang |
| 7,328,066 | B1 | 2/2008 | Levine |
| 7,440,803 | B2 | 10/2008 | Ni et al. |
| 7,474,916 | B2 | 1/2009 | Gutierrez |
| 7,653,436 | B2 | 1/2010 | Schecter |
| 7,890,163 | B2 | 2/2011 | Belalcazar |
| 8,019,409 | B2 | 9/2011 | Rosenberg et al. |
| 2006/0241703 | A1 | 10/2006 | Ding et al. |
| 2006/0247703 | A1* | 11/2006 | Gutierrez ............... 607/17 |
| 2006/0293714 | A1 | 12/2006 | Salo et al. |
| 2007/0043394 | A1 | 2/2007 | Zhang et al. |
| 2007/0129781 | A1 | 6/2007 | Yu et al. |
| 2007/0162080 | A1 | 7/2007 | Brockway et al. |
| 2008/0097539 | A1 | 4/2008 | Belalcazar |
| 2008/0269819 | A1 | 10/2008 | Zhou |
| 2009/0043218 | A1 | 2/2009 | Warner et al. |
| 2009/0204163 | A1 | 8/2009 | Shuros et al. |
| 2010/0121397 | A1* | 5/2010 | Cholette ............... 607/17 |
| 2010/0280401 | A1 | 11/2010 | Li |
| 2011/0077540 | A1 | 3/2011 | Belalcazar |
| 2011/0118803 | A1 | 5/2011 | Hou et al. |

OTHER PUBLICATIONS

Mercando, et al., "Measurement of Differences in Timing and Sequence Between Two Ventricular Electrodes as a Means of Tachycardia Differentiation", PACE, Part II, vol. 9, (Nov.-Dec. 1986), 1069-1078.

Tournoux, M.D., Francois, et al., "Concordance Between Mechanical and Electrical Dyssynchrony in Heart Failure Patients: A Funicton of the Underlying Cardiomyopathy?", Journal of Cardiovascular Electrophysiology vol. 18, No. 10, (Oct. 2007), 1022-1027.

\* cited by examiner

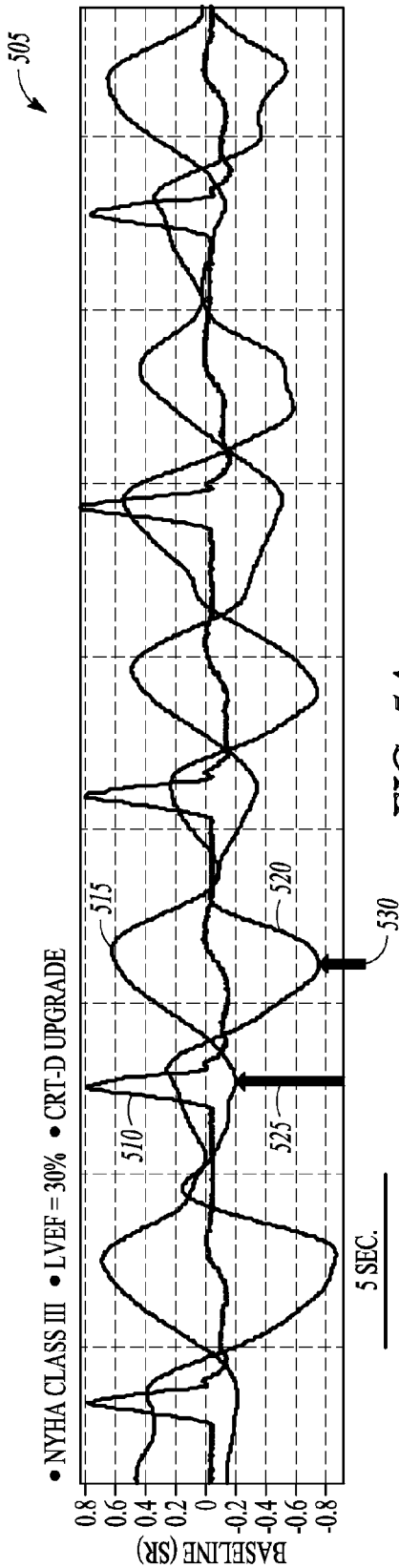
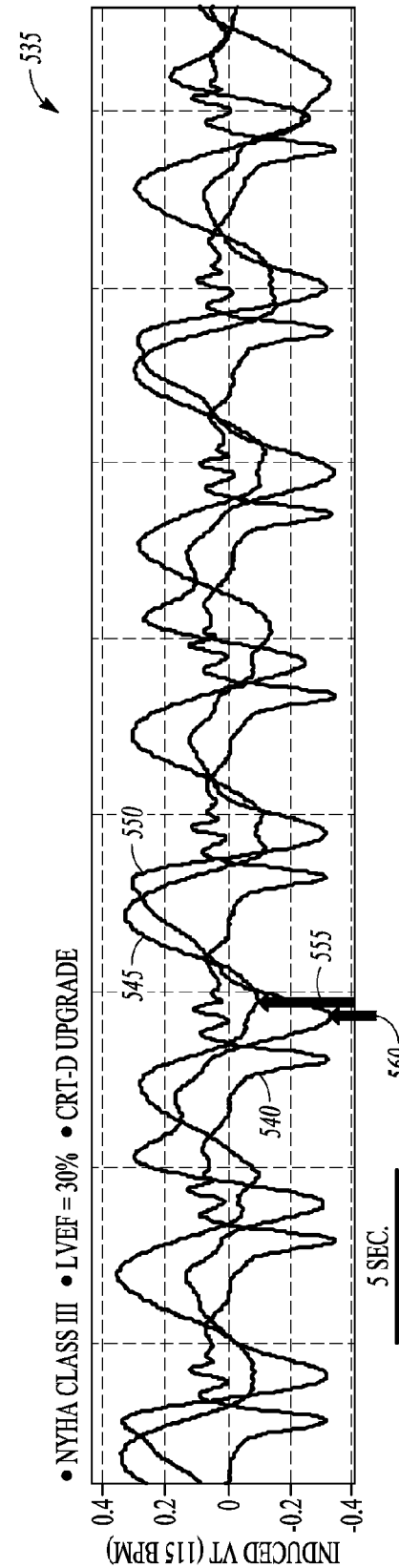

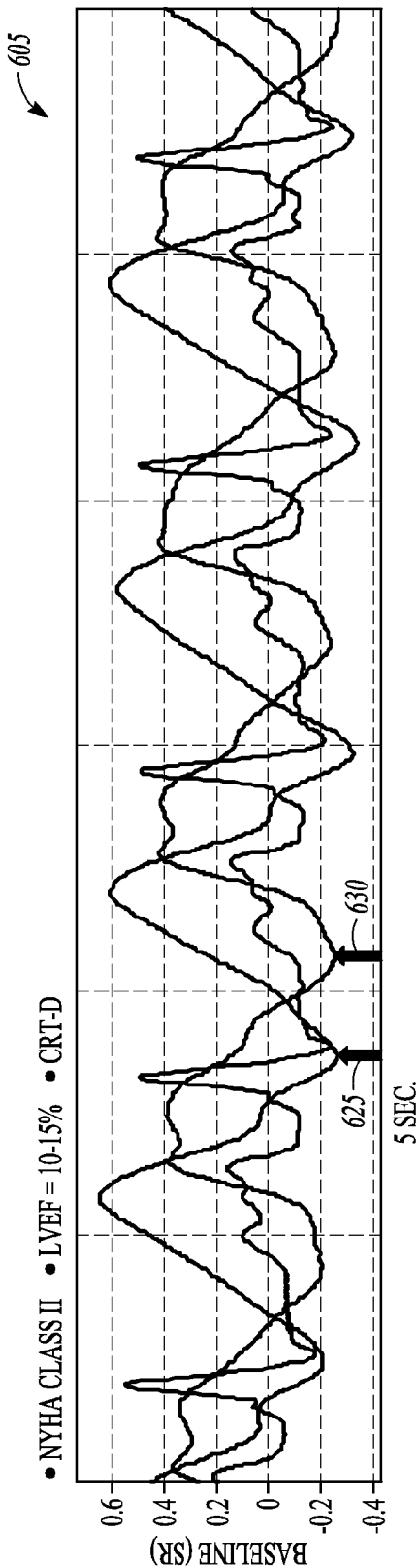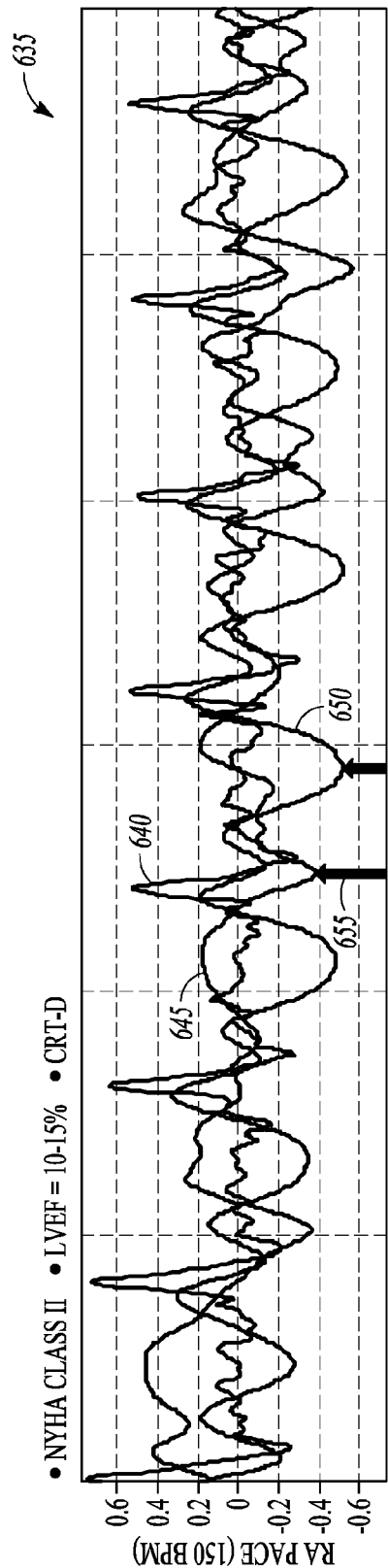
FIG. 6A
FIG. 6B

SYSTEMS AND METHODS OF CHARACTERIZING MECHANICAL ACTIVATION PATTERNS FOR RHYTHM DISCRIMINATION AND THERAPY

CLAIM OF PRIORITY

This application claims the benefit of priority under 35 U.S.C. §119(e) of Dan Li, U.S. Provisional Patent Application Ser. No. 61/605,936, entitled "SYSTEMS AND METHODS OF CHARACTERIZING MECHANICAL ACTIVATION PATTERNS FOR RHYTHM DISCRIMINATION AND THERAPY", filed on Mar. 2, 2012, which is herein incorporated by reference in its entirety.

BACKGROUND

Ambulatory medical devices include implantable medical devices (IMDs) and wearable medical devices (WMDs). Some examples of these implantable medical devices (IMDs) include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of IMDs include implantable diagnostic devices, implantable drug delivery systems, or implantable devices with neural stimulation capability.

WMDs include wearable cardioverter defibrillators (WCDs) and wearable diagnostic devices (e.g., an ambulatory monitoring vest). WCDs can be monitoring devices that include surface electrodes. The surface electrodes are arranged to provide one or both of monitoring to provide surface electrocardiograms (ECGs) and delivering cardioverter and defibrillator shock therapy.

Some medical devices detect events by monitoring electrical heart activity signals. In CFM devices, these events can include electrical cardiac activity. By monitoring cardiac electrical signals, IMDs can detect abnormally slow heart rate, or bradycardia. Some IMDs detect abnormally rapid heart rate, or tachyarrhythmia. Tachyarrhythmia includes ventricular tachycardia (VT) and supraventricular tachycardia (SVT). Tachyarrhythmia also includes rapid and irregular heart rate, or fibrillation, including ventricular fibrillation (VF).

When detected, tachyarrhythmia can be terminated with high energy shock therapy using an ICD or WCD. Underdetection of tachyarrhythmia (i.e., the device does not recognize an episode of tachyarrhythmia) may leave tachyarrhythmia untreated. Additionally, over-detection of tachyarrhythmia by a device (i.e., the IMD categorizes too many false-positives as tachyarrhythmia) is undesirable for the patient and the device. Cardioversion/defibrillation therapy can cause patient discomfort and consumes a relatively large amount of battery power which may lead to a shortened useful device lifetime. Therefore, it is important to accurately detect tachyarrhythmia.

OVERVIEW

Systems and methods for performing rhythm discrimination that includes confirming the type of event based on the mechanical and electrical activity signals are described in U.S. Patent Application Publication No. 2009/0204163, filed Feb. 5, 2009. A description of devices and methods for therapy control based on electromechanical timing can be found in U.S. Patent Application Publication No. 2006/0293714, filed Jun. 28, 2005.

Systems, devices, and methods that can provide electrical pacing therapy to the heart of a patient or subject are described herein. Such systems, devices, and methods can determine the decision making process for whether to deliver anti-tachyarrhythmia therapy and, if so, when to deliver therapy and what type of therapy to deliver (e.g., anti-tachyarrhythmia pacing (ATP) or defibrillation shock therapy).

An apparatus example can include an implantable sensor circuit that can be configured to generate a first sensor signal (other than an intrinsic electrical signal) representative of mechanical activation of a first chamber of a heart of a subject. A second sensor signal (also other than an intrinsic electrical signal) can be generated, representative of mechanical activation of a second chamber of the heart. A chamber synchrony measurement circuit can be configured to generate a measure of synchrony of the mechanical activations of the first heart chamber and the second heart chamber using the first and second sensor signals. A tachyarrhythmia detector circuit can be included. A control circuit can be communicatively coupled to the implantable sensor circuit, the chamber synchrony measurement circuit, and the tachyarrhythmia detector circuit. The control circuit can be configured to receive an indication of a detected episode of tachyarrhythmia. The control circuit can select a device-based therapy according to the measure of synchrony of the mechanical activations in response to the tachyarrhythmia detection.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

FIGS. 5A and 5B show graphs of more examples of monitoring mechanical activation of the heart using intracardiac impedance signals.

FIGS. 6A-C shows graphs of further examples of monitoring mechanical activation of the heart using intracardiac impedance signals.

DETAILED DESCRIPTION

Systems and methods for improved detection of tachyarrhythmia for a patient or subject are described herein.

Contractility of one or both of the right and left ventricles can deteriorate during VT. This deterioration in contractility can be reflected in the performance of the patient's hemodynamic system. For example, the change in contractility can prevent the heart chambers from filling properly; resulting in a drop in a patient's blood pressure. In some types of tachyarrhythmia (e.g., SVT), the heart rate becomes rapid but a patient's hemodynamic system remains stable. This is because the heart rate may remain regular enough so that the heart chambers are able to fill adequately and contract adequately to maintain adequate blood pressure. If a medical device identifies an episode of tachyarrhythmia with unstable hemodynamics, high energy cardioversion or defibrillation therapy can be delivered immediately. If the hemodynamic performance of the subject remains stable during the tachyarrhythmia, treatment can be delayed or an alternative treatment such as antitachyarrhythmia pacing (ATP) can be attempted before resorting to the high energy therapy, such as a defibrillation shock, which may cause patient discomfort. A proper assessment of mechanical activation patterns during a detected arrhythmia can be useful in making a decision in whether to deliver or to delay treatment when detecting a tachyarrhythmia.

Figure 1:
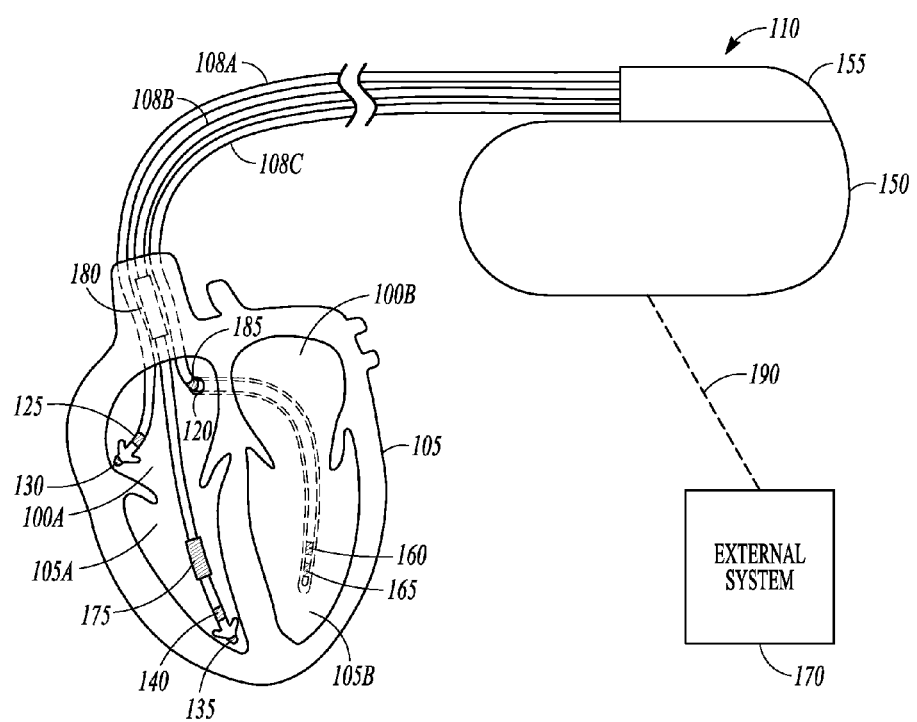
FIG. 1 is an illustration of an example of portions of a system that can include or use an IMD.

FIG. 1 is an illustration of portions of a system that uses an IMD 110. Examples of IMD 110 can include, without limitation, a pacemaker, a defibrillator, a cardiac resynchronization therapy (CRT) device, or a combination of such devices. The system 100 can also include an IMD programmer or other external device 170 that can communicate a wireless signal 190 with the IMD 110, such as by using radio frequency (RF) or another telemetry signal.

The IMD 110 can be coupled by one or more leads 108A-C to a heart 105. Cardiac leads 108A-C include a proximal end that can be coupled to the IMD 110 and a distal end that can be electrically coupled by one or more electrical contacts or "electrodes" to one or more portions of the heart 105. The electrodes can be used to deliver cardioversion, defibrillation, pacing, or resynchronization therapy, or one or more combinations thereof to at least one chamber of the heart 105. The electrodes can be electrically coupled to one or more sense amplifiers, which can be used to sense one or more electrical signals such as one or more intrinsic electrical cardiac signals.

A sensed electrical cardiac signal can be sampled to create an electrogram. The electrogram can be analyzed by the IMD. The electrogram can be stored in the IMD and communicated in real-time or after a delay to an external device, which can analyze or display the electrogram.

The heart 105 includes, among other things, a right atrium 100A, a left atrium 100B, a right ventricle 105A, a left ventricle 105B, and a coronary sinus 120 extending from right atrium 100A through the myocardium of the left ventricle 105B. A right atrial (RA) lead 108A can include one or more electrodes (electrical contacts, such as a ring electrode 125 and a tip electrode 130) that can be sized, shaped, located on the lead, or otherwise configured to be disposed in an atrium 100A of the heart 105 for sensing one or more electrical signals, or delivering pacing or other therapy, or both, to or from the atrium 100A.

The right ventricular (RV) lead 108B can include one or more electrodes, such as a tip electrode 135 and a ring electrode 140, that can be sized, shaped, located on the lead, or otherwise configured to be disposed in the right ventricle 105A of the heart 105, such as for sensing one or more electrical signals, delivering pacing or other therapy, or both, to or from the right ventricle 105A. The RV lead 108B can optionally also include one or more additional electrodes, such as for delivering atrial cardioversion, atrial defibrillation, ventricular cardioversion, ventricular defibrillation, or a combination thereof to the heart 105. Such additional cardioversion or defibrillation electrodes can have larger surface areas than pacing electrodes in order to handle the larger energies involved in cardioversion or defibrillation.

The lead 108B can include a first defibrillation coil electrode 175 that can be located proximal to the tip and ring electrodes 135, 140, such as for placement in a right ventricle (RV). The lead 108B can include a second defibrillation coil electrode 180 that can be located proximal to the RV coil 175, tip electrode 135, and ring electrode 140, such as for placement in the superior vena cava (SVC). In some examples, high-energy shock therapy can be delivered from the first or RV coil 175 to the second or SVC coil 180. In some examples, the SVC coil 180 can be electrically tied to another electrode, such as an electrode located at the hermetically-sealed IMD housing or can 150. This can improve defibrillation by delivering current from the RV coil 175 more uniformly over the ventricular myocardium. In some examples, the therapy can be delivered from the RV coil 175 to the electrode formed on the IMD can 150, which need not be electrically tied to the SVC coil electrode 180. In some examples, the coil electrodes 175, 180 can be used in combination with one or more other electrodes, such as for sensing one or more intrinsic cardiac or other electrical signals.

The lead 108B can optionally be used to provide cardiac resynchronization therapy (CRT) to the heart 105. CRT can be delivered to both ventricles in order to better synchronize the timing of depolarizations or contractions between ventricles, or CRT can be delivered to a single ventricle to spatially coordinate a contraction within that single ventricle. A third cardiac lead 108C can also be included and attached to the IMD 110 at the header 155. The third cardiac lead 108C can include electrodes 160 and 165 that can be sized, shaped, located on the lead, or otherwise configured to be placed in a coronary vein within the myocardial tissue of the left ventricle (LV) 105B, and can include one, two, three, four, or another number of ring electrodes.

Figure 2:
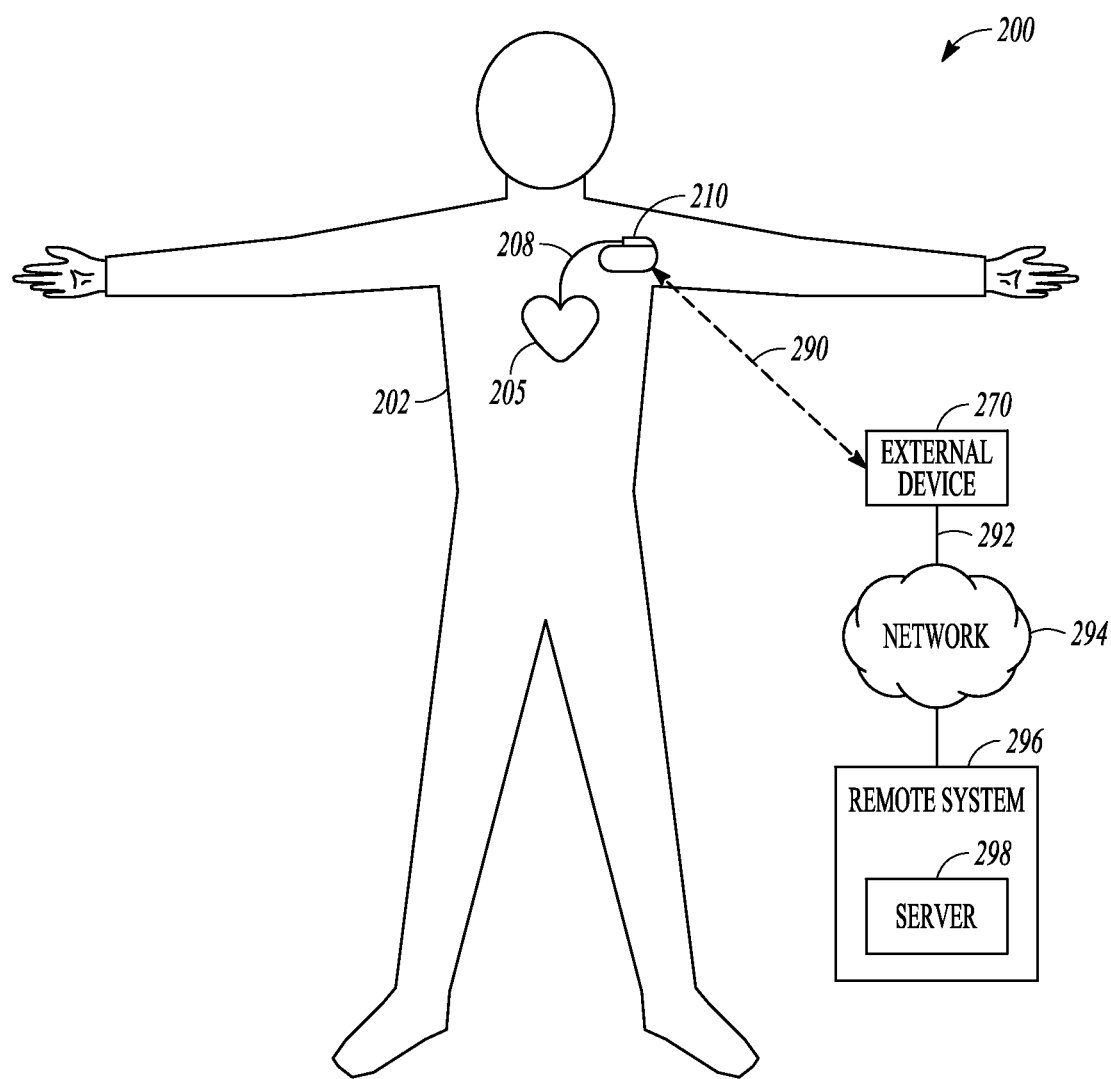
FIG. 2 is an illustration of portions of a system that can include or use an IMD.

FIG. 2 is an illustration of portions of a system 200 that can use an IMD 210, such as to monitor a patient 202 or to provide a therapy to the patient 202. The system 200 can include an external device 270 that can communicate one or more wireless signals 290 with the IMD 210. The external device 270 can also be configured to communicate with a remote system 296, such as via a network 294. The network 294 can include a communication network, such as a telephone network or a computer network (e.g., the internet). The external device 270 can include a repeater and can communicate via the network using a wired or wireless link 292. The remote system 296 can be configured to provide patient monitoring, device monitoring or programming, or one or more other functions, and can include or use one or more computer servers 298 or other devices to perform such functions.

Assessing mechanical contractility of the heart can be useful in making a decision in whether to deliver or to delay treatment of a detected tachyarrhythmia, as explained herein. For patients with heart failure, SVT and VT result in different mechanical activation sequences. For normal sinus rhythm (NSR) and SVT, the mechanical activation of the RV leads (e.g., occurs earlier in time than) the mechanical activation of the LV. This is because conduction delay is more significant on the left side of the heart. About one third of congestive heart failure (CHF or HF) patients have left bundle branch block (LBBB). During VT, the mechanical activation order can be reversed, such that mechanical activation of the LV leads mechanical activation of the RV. This is because many episodes of VT originate in the LV and propagate to the RV.

Also, for NSR and SVT, mechanical activation of the atrium (e.g., RA) leads activation of the ventricle (e.g., RV). However for VT, mechanical activation of the ventricle leads mechanical activation of the atrium, or the mechanical activations of the ventricle and atrium are disassociated. Thus, monitoring mechanical activation patterns of one or more of the RV-LV and A-V can provide useful information concerning a detected tachyarrhythmia. Such information can be actionable in a therapy decision or therapy control.

A mechanical activation pattern can be detected using a physiological sensor. Examples of physiological sensors suitable for mechanical activation pattern monitoring can include, among other things, an intracardiac pressure sensor or an intracardiac impedance sensor. Such mechanical activation pattern sensors can respectively provide signals that represent the mechanical functionality of the cardiovascular system. It should be noted that such mechanical activation pattern sensing is different from sensing electrical intrinsic cardiac signals, which are the intrinsic cardiac action potentials that propagate through the heart's electrical conduction system.

Figure 3:
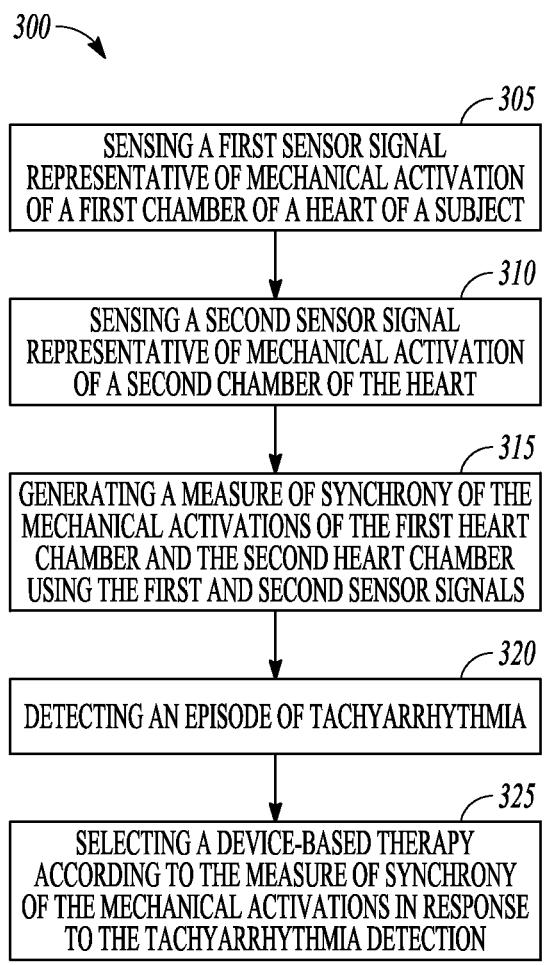
FIG. 3 is a flow diagram of an example of a method of operating a medical device.

FIG. 3 shows an example of a method 300 of operating a medical device. At 305, a first sensor signal (other than an intrinsic electrical signal) representative of mechanical activation of a first chamber of the heart of a subject can be sensed using the medical device.

At 310, a second sensor signal (also other than an intrinsic electrical signal) representative of mechanical activation of a second chamber of the heart can be sensed. In some examples, the medical device can be an implantable medical device (IMD) and the first and second sensor signals can be representative of intracardiac impedance of the subject. Intracardiac impedance refers to impedance sensed within a heart chamber in contrast to sensing impedance across the transthoracic region of the subject which can include a representation of respiration in the sensed signal.

In some examples, the first and second sensor signals can be representative of intracardiac pressure of the subject, or other intracardiac conductivity characteristic of the subject, from which mechanical cardiac activation information can be extracted.

Figure 4A:
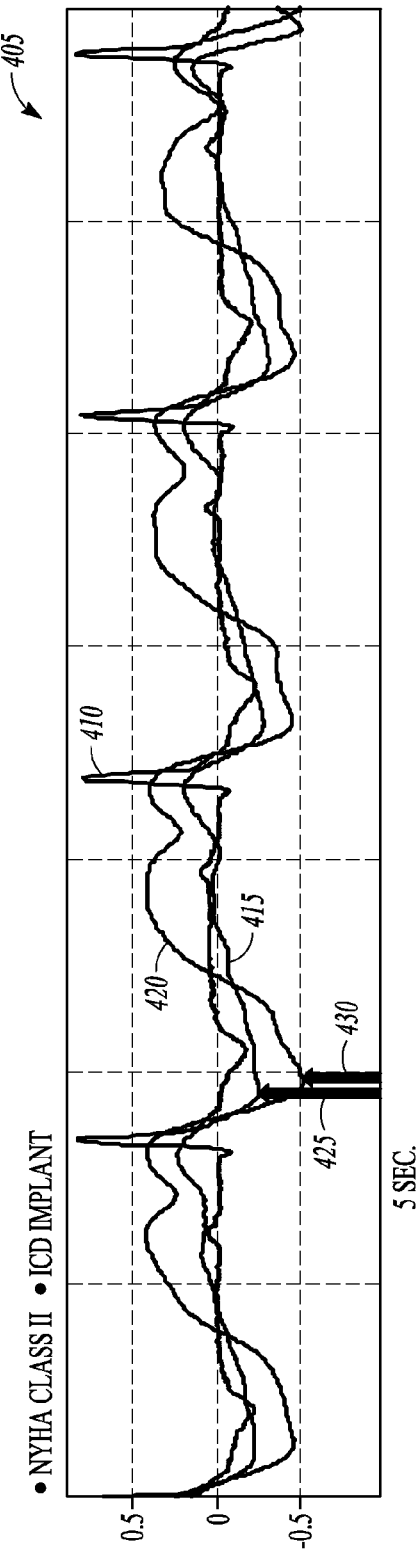
FIGS. 4A and 4B show graphs of examples of monitoring mechanical activation of the heart using intracardiac impedance signals.
Figure 4B:
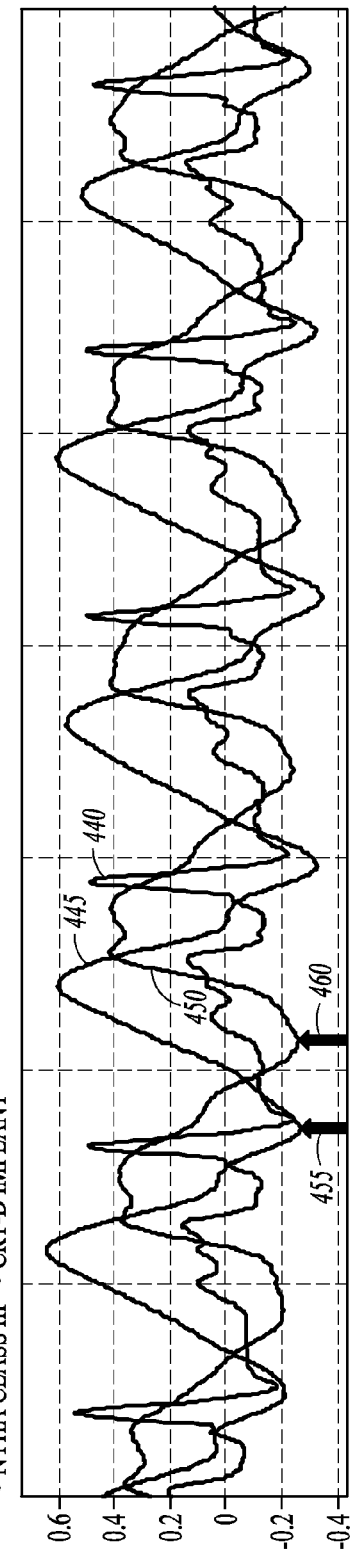

FIGS. 4A and 4B show examples of monitoring mechanical activation of the heart using intracardiac impedance signals. The graph 405 in FIG. 4A is an example for a patient with New York Heart Association (NYHA) Class II heart failure. The graph 405 illustrates an electrocardiograph (ECG) signal 410, a first intracardiac impedance signal 415 sensed for the right ventricle (RV) and a second intracardiac impedance signal 420 sensed for the left ventricle (LV). The RV intracardiac impedance signal was measured using between an RV coil electrode (such as RV coil electrode 175 in FIG. 1) and an SVC coil electrode (such as electrode 180 in FIG. 1). The LV intracardiac impedance signal was sensed between an RV tip electrode (such as electrode 135 in FIG. 1) and an LV tip electrode (such as electrode 165 in FIG. 1).

The first arrow 425 shown in the graph 405 of FIG. 4A identifies a trough in the RV impedance indicating a time of pre-ejection of the RV. The second arrow 430 identifies a trough in the LV impedance and indicates a time of pre-ejection of the LV. The order of the arrows indicate that pre-ejection of the RV precedes pre-ejection of the LV.

The graph 435 in FIG. 4B is an example for a patient with NYHA Class III heart failure. The graph 435 again includes an ECG signal 440, a first intracardiac impedance signal 445 sensed for the RV and a second intracardiac impedance signal 450 sensed for the LV. The arrows 455, 460 identify troughs in the RV intracardiac impedance signal and the LV intracardiac impedance signal respectively. The order of the arrows indicate that pre-ejection of the RV precedes pre-ejection of the LV. Note that the intracardiac impedance signals provide mechanical activation information that is distinct from the intrinsic electrical signals of the ECGs.

Returning to FIG. 3 at 315, a measure of synchrony of the mechanical activations of the first heart chamber and the second heart chamber can be generated, such as by using the first and second sensor signals. An example of the measure of synchrony is the time interval between pre-ejection of the RV and pre-ejection of the LV (e.g., the time between the arrows in the graphs of FIG. 4).

At 320, an episode of tachyarrhythmia can be detected, such as by extracting heart rate or other information from a sensed intrinsic electrical signal of the ECG or from the mechanical activation information that is distinct from such intrinsic electrical signal of the ECG. In some examples, the tachyarrhythmia episode can be declared when the heart rate exceeds a tachyarrhythmia rate detection threshold value.

At 325, a device-based therapy can selected, such as using information about the measure of synchrony of the mechanical activations, which can be obtained in response to the tachyarrhythmia detection declaring that a tachyarrhythmia episode is present.

FIGS. 5A and 5B show graphs of more examples of monitoring mechanical activation of the heart using intracardiac impedance signals. The graph 505 in FIG. 5A is another example for a patient with NYHA Class III heart failure. The graph 505 includes an ECG signal 510, a first intracardiac impedance signal 515 sensed for the RV and a second intracardiac impedance signal 520 sensed for the LV. The example in the top graph 505 represents regular sinus rhythm (SR) for the patient. The arrows 525, 530 identify troughs in the RV intracardiac impedance signal and the LV intracardiac impedance signal respectively corresponding to the time of pre-ejection for each ventricle. The order of the arrows indicate that pre-ejection of the RV precedes pre-ejection of the LV.

The graph 535 in FIG. 5B shows an episode of induced VT for the patient. The graph 535 again includes an ECG signal 540, a first intracardiac impedance signal 545 sensed for the RV and a second intracardiac impedance signal 550 sensed for the LV. The arrows 555, 560 correspond to troughs in the RV intracardiac impedance signal and the LV intracardiac impedance signal respectively to indicate the time of pre-ejection. The arrows show that for VT pre-ejection of the LV occurs before pre-ejection of the RV. If the measure of synchrony is the time interval between pre-ejection of the RV and pre-ejection of the LV, the measure of synchrony would have a positive value for regular sinus rhythm, but would change sign to a negative value when an episode of VT occurs.

Figure 6C:
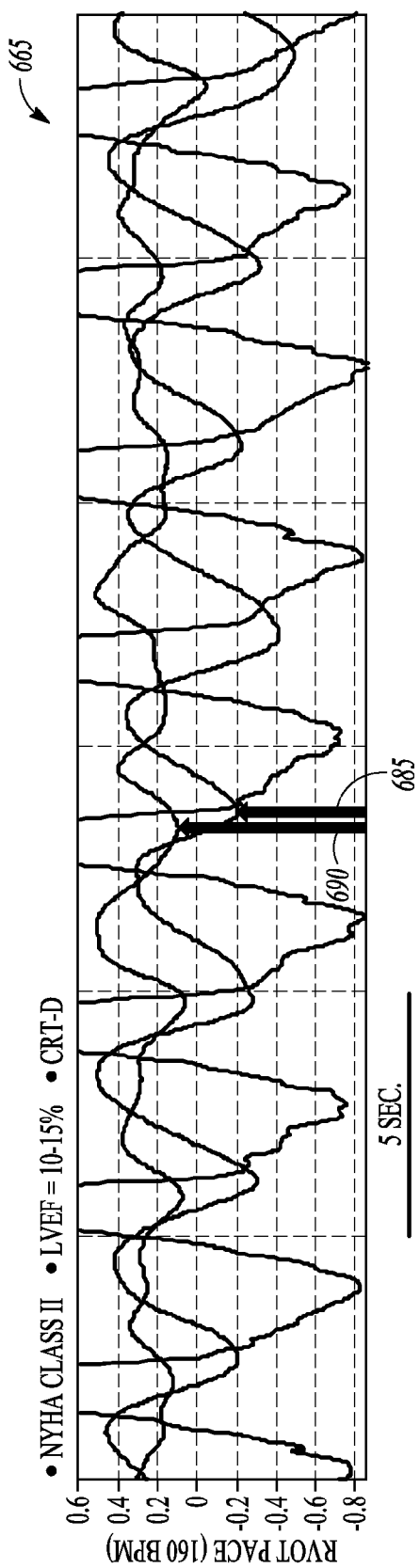

FIGS. 6A-6C show graphs of further examples of monitoring mechanical activation of the heart using intracardiac impedance signals. The graph 605 of FIG. 6A represents sinus rhythm for a patient with NYHA class II heart failure. The arrows 625, 630 indicate the time of pre-ejection for the RV and LV respectively.

The graph 635 of FIG. 6B results from rapidly pacing the RA (at 150 bpm) to artificially simulate SVT. The graph 635 includes an ECG signal 640, an RV intracardiac impedance signal 645, and an LV intracardiac impedance signal 650. The arrows 655, 660 represent the time of pre-ejection for the RV and LV respectively, and show that pre-ejection of the RV still leads pre-ejection of the LV during the simulated SVT.

The graph 665 of FIG. 6C represents VT induced in the patient. The arrows 685, 690 again represent the time of pre-ejection for the RV and LV respectively and again show that mechanical activation of the LV occurs prior to mechanical activation of the RV during VT.

The several graphs illustrated herein demonstrate that monitoring mechanical activation of the heart can lead to detecting changes in cardiac mechanical synchrony, information from which can be used to recognize or discriminated between different types of cardiac arrhythmias. Using a medical device to determine the mechanical activation sequence between RV-LV heart chambers or between A-V heart chambers (such as by monitoring multiple intracardiac impedance vectors as in the graphs of the figures) can provide advantages in better treating the patient. The graphs demonstrate how mechanical activation information can be used to differentiate SVT and VT.

Monitoring the sequence of mechanical activation can also be used to determine the origin of detected VT. For instance, for an episode of VT originating in the septum of the heart, the delay between mechanical activation of the LV to mechanical activation of the RV may be shorter than when the episode originates in the LV. Therefore, there may be less measured separation between mechanical activation of the LV and RV for VT originating in the septum than for VT originating in the LV. Information about cardiac mechanical activation can lead to improved device-based decisions controlling the type or timing or other parameters of therapy that can be provided by the device to treat a detected tachyarrhythmia.

Figure 7:
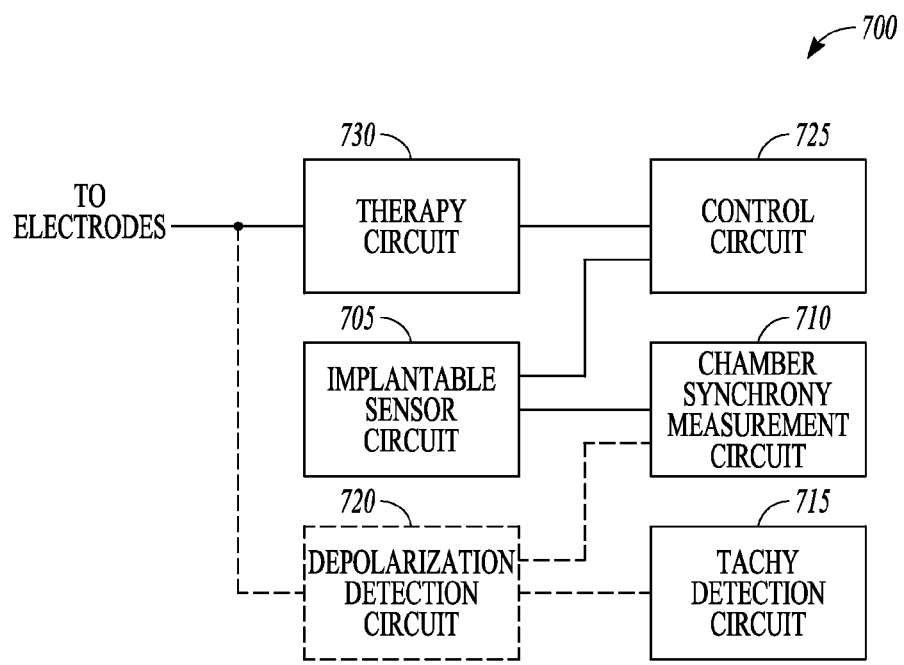
FIG. 7 is a block diagram of portions of an example of a device to mechanical activation of a heart of a subject.

FIG. 7 is a block diagram of portions of an example of a device 700 that can be used to monitor mechanical activation of a heart of a subject. The device 700 can include an implantable sensor circuit 705 that can generate a first sensor signal (other than an intrinsic electrical signal) representative of mechanical activation of a first chamber of a heart of a subject, and a second sensor signal (also other than an intrinsic electrical signal) representative of mechanical activation of a second chamber of the heart.

In some examples, the implantable sensor circuit 705 can include an intracardiac impedance (or other intracardiac conductivity characteristic) sensing circuit that can be configured to provide a first intracardiac impedance signal sensed for the first heart chamber as the first sensor signal, and provides a second intracardiac impedance signal sensed for the second heart chamber as the second sensor signal.

The intracardiac impedance sensing circuit can be coupled to implantable electrodes to obtain an intracardiac impedance signal, such as by applying a specified (e.g., subcapture) excitation current to cardiac tissue, and sense a voltage signal resulting from the test current. The voltage response can (but need not) be sensed using the same electrodes as those used to deliver the test current. Ohm's Law (R=V/I) can then be used to derive the intracardiac impedance signal. To avoid unintended capture of the heart or to avoid unwanted ECG signal artifacts, the magnitude of the applied excitation current can be small (e.g., 1-2 microamperes), the pulse width of the applied excitation current can be small (e.g., 1 milliamperes amplitude, 15 microsecond pulse width, 47 millisecond period), and/or a high frequency test excitation can be used.

In some examples, the first intracardiac impedance signal can be representative of intracardiac impedance of the LV and second intracardiac impedance signal can be representative of intracardiac impedance of the RV. In some examples, the intracardiac impedance can be sensed using a unipolar electrode configuration. For instance, the first intracardiac impedance signal can be sensed between an LV electrode (e.g., LV tip electrode 165 in FIG. 1) and an electrode formed on a can or header of a pectorally-implanted or otherwise located device 700. The second intracardiac impedance signal can be sensed between an RV electrode (e.g. RV tip electrode 135) and an electrode formed on the can or header of the pectorally-implanted or otherwise located device 700. Because of the unipolar configuration, the intracardiac impedance measurement may include a DC or a near-DC (e.g., frequencies less than 0.1 Hz) component. It certain examples, the intracardiac impedance sensing circuit can include a filter circuit to filter this component out of a sensed intracardiac impedance signal.

In some examples, the intracardiac impedance can be sensed using a bipolar electrode configuration. For instance, the first intracardiac impedance signal can be sensed between LV tip electrode 165 and LV ring electrode 160 shown FIG. 1, or between the LV tip electrode and either the RV tip electrode 135 or the RV ring electrode 140. The second intracardiac impedance signal can be sensed between an RV tip electrode 135 and any of RV ring electrode 140, RA tip electrode 130, or RA ring electrode 125, or sensed between RV coil electrode 175 and SVC coil electrode 180.

Intracardiac impedance can additionally or alternatively be used to monitor A-V mechanical synchrony. The first intracardiac impedance signal can be representative of intracardiac impedance of the RA, such as by measuring impedance between an electrode in the RA (e.g., RA tip electrode 130, or RA ring electrode 125 in FIG. 1) and an electrode formed on the can or header of a pectorally or otherwise located device 700. The second intracardiac impedance signal can be representative of intracardiac impedance of the RV and can be measured using any of the RV impedance vectors described herein.

In some examples, the implantable sensor circuit 705 of FIG. 7 can include an intracardiac pressure sensing circuit that can provide a first intracardiac pressure signal sensed for the first heart chamber as the first sensor signal. The intracardiac pressure sensing circuit can provide a second intracardiac pressure signal sensed for the second heart chamber as the second sensor signal. An implantable intracardiac pressure sensor can be used to measure chamber pressure of a ventricle (e.g., the left ventricle). For instance, a pressure sensor can be implanted in a coronary vessel to determine LV pressure by direct measurement of coronary vessel pressure. Other placements of a pressure sensor can measure intracardiac pressure of the RV, RA, or left atrium (LA).

The device 700 can also include a chamber synchrony measurement circuit 710 that can be configured to generate a measure of synchrony of the mechanical activations of the first heart chamber and the second heart chamber using the first and second sensor signals. The measure of synchrony can include the time interval or time difference between onsets of the mechanical activation (e.g., the time interval between pre-ejection of the ventricles as indicated by the arrows in FIGS. 4-7), or the time interval or time difference between peak mechanical activation of the ventricles (e.g., peak mechanical contraction). The measure of synchrony can include a time delay between the onset of the mechanical activation of the first heart chamber and the onset of the mechanical activation of the second heart chamber. The measure of synchrony can include a delay between a time of peak amplitude of the first sensor signal and a time of peak amplitude of the second sensor signal. The measure of synchrony can be measured in the time domain or in the frequency domain. For instance, the measure of synchrony can include a time domain or frequency domain phase shift between the first sensor signal and the second sensor signal.

The device 700 can also include a tachyarrhythmia detector circuit 715. For instance, the device 700 can include a cardiac depolarization detector circuit 720 that can be configured to detect cardiac depolarization using a sensed intrinsic electrical cardiac signal. The tachyarrhythmia detector circuit 715 can be configured to declare a detected tachyarrhythmia when a detected rate of depolarizations exceeds a specified tachyarrhythmia detection rate threshold value, or when one or more intervals between depolarizations fall below a tachyarrhythmia detection interval threshold value.

The device 700 can further include a control circuit 725 and a therapy circuit 730. The control circuit 725 can be communicatively coupled to the implantable sensor circuit 705, the chamber synchrony measurement circuit 710, or the tachyarrhythmia detector circuit 715. The communicative coupling can allow one or more electrical signals to be communicated between the control circuit 725 and one or more of the implantable sensor circuit 705, the chamber synchrony measurement circuit 710, or the tachyarrhythmia detector circuit 715, either directly or via intervening circuitry.

The control circuit 725 can include a processor circuit, a digital signal processor (DSP) circuit, an application specific integrated circuit (ASIC), a microprocessor circuit, or other type of processor circuit, such as can interpret or execute or otherwise perform one or more instructions, such as using one or more software modules or firmware modules. For instance, the control circuit 725 can include a sequencer, such as a state machine or other circuit that sequentially steps through a fixed series of steps to perform one or more functions. The steps can be implemented using hardware or firmware. The control circuit 725 can include other circuits or sub-circuits to perform the functions described. These circuits may include software, hardware, firmware or any combination thereof. Multiple functions can be performed in one or more of the circuits, as desired.

The control circuit 725 can be communicatively coupled to the therapy circuit 730. The therapy circuit 730 can be configured to provide one or more of high energy defibrillation therapy, cardioversion therapy, anti-tachyarrhythmia pacing (ATP) therapy, or other therapy. The control circuit 725 can be configured to receive an indication of a detected episode of tachyarrhythmia and to select a device-based therapy at least in part using the measure of synchrony of the mechanical activations obtained during a tachyarrhythmia, such as in response to the tachyarrhythmia detection.

In some examples, the chamber synchrony measurement circuit 710 can be configured to provide a measure of heart chamber synchrony that can indicate a sequence of mechanical activation of the first and second heart chambers. The control circuit 725 can classify the detected tachyarrhythmia episode, for instance, as a supraventricular tachyarrhythmia (SVT) or as a ventricular tachyarrhythmia (VT), such as according to the measure of synchrony of the mechanical activations, as explained herein. The control circuit 725 can automatically select the device-based therapy at least in part according to the indicated sequence of mechanical activation. For instance, the control circuit 725 can initiate defibrillation therapy if the measure of synchrony indicates that the tachyarrhythmia is VT. If the measure of synchrony indicates that mechanical activation of the chambers is still properly synchronized during the VT episode, the control circuit can delay defibrillation therapy, such as to see whether the VT is resolved by the heart on its own, or the control circuit 725 can initiate ATP therapy to convert the tachyarrhythmia back to proper sinus rhythm, for instance, instead of or before delivering a defibrillation.

In some examples, the implantable sensor circuit 705 can be configured to provide a signal representative of mechanical activation of the LV of the heart as the first sensor signal, and to provide a signal representative of mechanical activation of the RV of the heart as the second sensor signal. The control circuit 725 can classify the detected tachyarrhythmia episode as SVT when the measure of synchrony indicates that mechanical activation of the LV lags mechanical activation of the RV, and can classify the detected tachyarrhythmia episode as VT when the measure of synchrony indicates that the mechanical activation of the LV leads the mechanical activation of the RV. For instance, if the first sensor signal is representative of LV intracardiac impedance ($Z_{LV}$) and the second sensor signal is representative of RV intracardiac impedance ($Z_{RV}$), then the control circuit 725 can classify the tachyarrhythmia episode as SVT when $Z_{LV}$ lags $Z_{RV}$, and can classify the episode as VT when $Z_{LV}$ leads $Z_{RV}$.

For the case where the mechanical activation appears to be simultaneous, the control circuit 725 can be configured to interpret the arrhythmia as VT to ensure that VT is treated. In some examples, the control circuit 725 is configured to interpret an arrhythmia as VT when the mechanical activation of each of the heart chambers occurs within a specified time value.

In some examples, the implantable sensor circuit 705 can provide a signal representative of mechanical activation of the RA of the heart as the first sensor signal and can provide a signal representative of mechanical activation of the RV of the heart as the second sensor signal. The control circuit 725 can classify the tachyarrhythmia episode as SVT when the measure of synchrony indicates that mechanical activation of the RA leads mechanical activation of the RV, and can classify the tachyarrhythmia episode as VT when the measure of synchrony indicates that the mechanical activation of the RA lags the mechanical activation of the RV. For instance, if the first sensor signal is representative of RA intracardiac impedance ($Z_{RA}$) and the second sensor signal is representative of RV intracardiac impedance ($Z_{RV}$), then the control circuit can classify the tachyarrhythmia episode as SVT when $Z_{RA}$ leads $Z_{RV}$ and can classify the episode as VT when $Z_{RA}$ lags $Z_{RV}$.

In some examples, the control circuit 725 can be configured to determine which heart chamber originated the episode of tachyarrhythmia, such as using information about the measure of synchrony of mechanical activations, and can select the device-based therapy at least in part using the determined heart chamber of tachyarrhythmia origin. For instance, as explained previously herein, there may be less measured separation between mechanical activation of the LV and RV for VT originating in the septum than for VT originating in the LV. Thus, the control circuit 725 can detect VT when the mechanical activation of the LV leads the mechanical activation of the RV and determine that the tachyarrhythmia originated in the LV instead of the septum when the measured delay between mechanical activation of the LV and RV heart chambers is greater than a specified delay value. Similarly for RA-RV monitoring, the control circuit 725 can determine that tachyarrhythmia originated in the LV instead of the septum when the measured delay between mechanical activation of the RV and RA heart chambers is greater than a specified delay value.

In some examples, the chamber synchrony measurement circuit 710 can be configured to calculate a baseline value for the measure of synchrony of mechanical activations. For instance, a mean, median, or other central tendency of the measure can be determined over several cardiac cycles of NSR. The control circuit 725 can be configured to schedule a delivery of a device-based therapy at least in part using information about the detected tachyarrhythmia, such as a detected change in the measure of synchrony of mechanical activations from the calculated baseline value. In response to such a detected change in the measure of synchrony of mechanical activations, the control circuit 725 can initiate or adjust at least one of a type of device-based therapy, or a scheduled delivery time of the device based therapy.

The measure of heart chamber mechanical synchrony can be normalized or otherwise adjusted, e.g., with respect to heart rate during the detected tachyarrhythmia, such as to account for the impact of the change in heart rate on the measure of heart chamber mechanical synchrony, which is a fraction of the interval between successive heart contractions. For instance, the device 700 can include the cardiac depolarization detector circuit 720, and the chamber synchrony measurement circuit 710 can determine a heart rate of the subject using the interval between detected cardiac depolarizations. The chamber synchrony measurement circuit 710 can be configured to measure at least one of i) a time delay between onset of the mechanical activation of the first heart chamber and onset of the mechanical activation of the second heart chamber, with the time delay normalized with respect to a determined heart rate or heart rate interval, or ii) the time delay between a time of peak amplitude of the first sensor signal and a time of peak amplitude of the second sensor signal, with the time delay normalized with respect to the determined heart rate or heart rate interval. The chamber synchrony measurement circuit 710 can be configured to provide the least one of the normalized measured time delay between the onsets or the normalized measured delay between times of peak amplitude as a measure of synchrony of the mechanical activations.

A normalized measure of heart chamber synchrony, such as described herein, can be used to assess the hemodynamic performance of the patient during the tachyarrhythmia. Although heart rate during a tachyarrhythmia may play a dominant role in deciding hemodynamic outcome, dyssynchrony of the heart chambers (e.g., RV-LV dyssynchrony or A-V dyssynchrony) can increase as hemodynamic performance further deteriorates during a tachyarrhythmia episode. An indication of increased dyssynchrony (e.g., as reflected by the normalized or other measure of mechanical synchrony) can indicate that the patient should immediately receive defibrillation therapy from the device, rather than delaying such defibrillation therapy to await spontaneous resolution or to deliver ATP. A normalized mechanical measure of heart chamber synchrony can assist in rhythm discrimination by the device 700, can assist in assessing hemodynamic stability by the device 700, or can permit the device 700 to automatically adjust the therapy decision or one or more therapy parameters in response to detection of tachyarrhythmia. The adjustment in therapy decisions can include delaying the specified therapy when SVT is indicated, or when VT with a non-significant decay in hemodynamic performance is indicated. The adjustment in therapy can also include expediting a specified therapy if VT with significant decay in hemodynamic performance is indicated. One or more therapy delivery parameters (e.g., therapy energy) can also be adjusted using information obtained from the normalized or other mechanical measure of heart chamber synchrony.

In some examples, a combination of an intrinsic electrical cardiac signal and a mechanical activation signal can be used to classify a tachyarrhythmia, such as to create actionable information for selecting, initiating, or adjusting a therapy or therapy parameter. The intrinsic electrical cardiac signal can be used to detect a tachyarrhythmia episode, such as by heart rate exceeding a tachyarrhythmia rate detection threshold value, or by a morphological tachyarrhythmia detection or discrimination technique that can be applied to the intrinsic electrical cardiac signal. Analysis of one or more signals (e.g., different than intrinsic electrical cardiac signals, such as an impedance-indicating signal, a pressure-indicating signal, or the like) produced by one or more physiological sensors can then be used to identify the type of tachyarrhythmia, or can be used in combination with one or more sensed electrical intrinsic signals to identify the type of tachyarrhythmia. This combined analysis can further improve device-based decision making regarding treatment of tachyarrhythmia.

These several examples of devices and methods to classify tachyarrhythmia described herein demonstrate that monitoring mechanical cardiac activation can be used to help reduce unnecessary therapy, especially shock therapy, because such therapy is not delivered unless and until the therapy is deemed necessary using information about the mechanical cardiac activation. Providing shocks only when such therapy is necessary can help improve device-based therapy for the patient.

Additional Notes and Examples

Example 1 can include subject matter (such as an apparatus, a method, a tangible non-transitory device-readable medium for performing all or a portion of a method, or a means for performing certain acts) that can include or use an implantable sensor circuit, a chamber synchrony measurement circuit, a tachyarrhythmia detector circuit, and a control circuit. The implantable sensor circuit can be configured to generate a first sensor signal, other than an intrinsic electrical signal. The first sensor signal can be representative of mechanical activation of a first chamber of a heart of a subject. The implantable sensor circuit can be configured to generate a second sensor signal, also other than an intrinsic electrical signal. The second sensor signal can be representative of mechanical activation of a second chamber of the heart. A chamber synchrony measurement circuit can be configured to generate a measure of synchrony of the mechanical activations of the first heart chamber and those of the second heart chamber, such as using the first and second sensor signals. The control circuit can be communicatively coupled to implantable sensor circuit, the chamber synchrony measurement circuit, and the tachyarrhythmia detector circuit. The control circuit can be configured to receive an indication of a detected episode of tachyarrhythmia. The control circuit can be configured to select a device-based therapy according to the measure of synchrony of the mechanical activations, such as can be obtained in response to the tachyarrhythmia detection.

Example 2 can include or use, or can optionally be combined with the subject matter of Example 1 to optionally include or use, a control circuit that can be configured to classify the tachyarrhythmia episode as supraventricular tachyarrhythmia (SVT) or ventricular tachyarrhythmia (VT), such as at least in part using the measure of synchrony of the mechanical activations. The measure of synchrony can indicate a sequence of mechanical activation of the first and second heart chambers. The control circuit can be configured to select a device-based therapy at least in part using the indicated sequence of mechanical activation.

Example 3 can include or use, or can optionally be combined with the subject matter of one or any combination of Examples 1 and 2 to optionally include or use, an implantable sensor circuit that can be configured to provide a signal representative of mechanical activation of the left ventricle (LV) of the heart as the first sensor signal, and to provide a signal representative of mechanical activation of the right ventricle (RV) of the heart as the second sensor signal. The control circuit can optionally be configured to classify the detected tachyarrhythmia episode as SVT when the measure of synchrony indicates that mechanical activation of the LV lags mechanical activation of the RV, and to classify the detected tachyarrhythmia episode as VT when the measure of synchrony indicates that the mechanical activation of the LV leads the mechanical activation of the RV.

Example 4 can include or use, or can optionally be combined with the subject matter of one or any combination of Examples 1 through 3 to optionally include or use, an implantable sensor circuit that can be configured to provide a signal representative of a mechanical activation of the right atrium (RA) of the heart as the first sensor signal and to provide a signal representative of mechanical activation of the RV of the heart as the second sensor signal. The control circuit can optionally be configured to classify the tachyarrhythmia episode as SVT when the measure of synchrony indicates that mechanical activation of the RA leads mechanical activation of the RV, and to classify the tachyarrhythmia episode as VT when the measure of synchrony indicates that the mechanical activation of the RA lags the mechanical activation of the RV.

Example 5 can include or use, or can optionally be combined with the subject matter of one or any combination of Examples 1 through 4 to optionally include or use, a chamber synchrony measurement circuit that can be configured to calculate a baseline value for the measure of synchrony of mechanical activations. The control circuit can optionally be configured to schedule a delivery of a device-based therapy at least in part using information about the detected tachyarrhythmia, to detect a change in the measure of synchrony of mechanical activations from the calculated baseline value, and to change at least one of a type of device-based therapy or a time the delivery of the device based therapy is scheduled at least in part using the detected change in the measure of synchrony of mechanical activations.

Example 6 can include or use, or can optionally be combined with the subject matter of one or any combination of Examples 1 through 5 to optionally include or use, a control circuit that can be configured to determine which heart chamber originated the episode of tachyarrhythmia, such as at least in part using information about the measure of synchrony of mechanical activations, and to initiate, select, or adjust the device-based therapy at least in part using information about the determined heart chamber of tachyarrhythmia origin.

Example 7 can include or use, or can optionally be combined with the subject matter of one or any combination of Examples 1 through 6 to optionally include or use, an implantable sensor circuit that can include an intracardiac impedance sensing circuit. The intracardiac impedance sensing circuit can be configured to provide a first intracardiac impedance signal sensed for the first heart chamber as the first sensor signal, and to provide a second intracardiac impedance signal sensed for the second heart chamber as the second sensor signal.

Example 8 can include or use, or can optionally be combined with the subject matter of one or any combination of Examples 1 through 7 to optionally include or use, an implantable sensor circuit that can include an intracardiac pressure sensing circuit that can be configured to provide a first intracardiac pressure signal sensed for the first heart chamber as the first sensor signal, and to provide a second intracardiac pressure signal sensed for the second heart chamber as the second sensor signal.

Example 9 can include or use, or can optionally be combined with the subject matter of one or any combination of Examples 1 through 8 to optionally include or use, a chamber synchrony measurement circuit that can be configured to measure at least one of: a time delay between onset of the mechanical activation of the first heart chamber and onset of the mechanical activation of the second heart chamber, a delay between a time of peak amplitude of the first sensor signal and a time of peak amplitude of the second sensor signal, and a phase shift between the first sensor signal and the second sensor signal. The first and second sensor signals can be frequency domain signals. The chamber synchrony measurement circuit can be configured to provide the least one of the measured time delay between onsets, the measured delay between times of peak amplitude, and the measured phase shift as the measure of synchrony of the mechanical activations.

Example 10 can include or use, or can optionally be combined with the subject matter of one or any combination of Examples 1 through 9 to optionally include or use, a cardiac depolarization detector circuit. The chamber synchrony measurement circuit can optionally be configured to determine a heart rate of the subject, such as using detected cardiac depolarization, and to measure at least one of: (1) a measure of a time delay between onset of the mechanical activation of the first heart chamber and onset of the mechanical activation of the second heart chamber normalized with respect to a determined heart rate, and (2) a measure of a time delay between a time of peak amplitude of the first sensor signal and a time of peak amplitude of the second sensor signal, such as can be normalized, for instance, with respect to the determined heart rate. The chamber synchrony measurement circuit can further optionally be configured to provide the least one of the normalized measured time delay between onsets or the normalized measured delay between times of peak amplitude as the measure of synchrony of the mechanical activations.

Example 11 can include or use, or can optionally be combined with the subject matter of one or any combination of Examples 1-10 to include or use, subject matter (such as an apparatus, a method, a means for performing acts, or a device readable medium including instructions that, when performed by the device, can cause the device to perform acts) comprising sensing a first sensor signal, other than an intrinsic electrical signal, representative of mechanical activation of a first chamber of a heart of a subject using the implantable medical device, sensing a second sensor signal, also other than an intrinsic electrical signal, representative of mechanical activation of a second chamber of the heart, generating a measure of synchrony of the mechanical activations of the first heart chamber and the second heart chamber using the first and second sensor signals, detecting an episode of tachyarrhythmia, and initiating, selecting, or adjusting a device-based therapy at least in part using information about the measure of synchrony of the mechanical activations obtained in response to the tachyarrhythmia detection.

Such subject matter can include a means for sensing the first sensor signal and sensing the second sensor signal, illustrative examples of which can include an intracardiac impedance sensor and an intracardiac pressure sensor. Such subject matter can include means for generating a measure of synchrony of the mechanical activations of the first heart chamber and the second heart chamber using the first and second sensor signals, an illustrative example of which can include chamber synchrony measurement circuit configured to generate a measure of synchrony of the mechanical activations of the first heart chamber and the second heart chamber using the first and second sensor signals. The chamber synchrony measurement circuit can be integral to a control circuit or coupled to the control circuit. Such subject matter can include means for detecting an episode of tachyarrhythmia, illustrative examples of which can include a depolarization detection circuit to detect tachyarrhythmia using one or more of depolarization rate, rate interval, or rate stability, and a morphology comparison circuit to detect tachyarrhythmia using a comparison to a tachyarrhythmia rate. Such subject matter can include means for selecting a device-based therapy according to the measure of synchrony of the mechanical activations in response to the tachyarrhythmia detection, an illustrative example of which can include a control circuit configured through one or more of software, hardware, and firmware to perform the selection.

Example 12 can include or use, or can optionally be combined with the subject matter of Examples 1-11 to include or use, classifying the detected tachyarrhythmia episode as SVT or VT, such as at least in part using information about the measure of synchrony of the mechanical activations, wherein the measure of synchrony indicates a sequence of mechanical activation of the first and second heart chambers. A device-based therapy can be selected at least in part using information about the indicated sequence of mechanical activation.

Example 13 can include or use, or can optionally be combined with the subject matter of one or any combination of Examples 1-12 to include or use, a first sensor signal representative of mechanical activation of the LV of the heart and a second sensor signal representative of mechanical activation of the RV of the heart. Classifying the tachyarrhythmia episode as SVT or VT can optionally include classifying the tachyarrhythmia episode as SVT when the measure of synchrony indicates that mechanical activation of the LV lags mechanical activation of the RV, and classifying the tachyarrhythmia episode as VT when the measure of synchrony indicates that the mechanical activation of the LV leads the mechanical activation of the RV.

Example 14 can include or use, or can optionally be combined with the subject matter of one or any combination of Examples 1 through 13 to include or use, a first sensor signal representative of mechanical activation of the RA of the heart and a second sensor signal representative of mechanical activation of the RV. Classifying the tachyarrhythmia episode as SVT or VT can optionally include or use classifying the tachyarrhythmia episode as SVT when the measure of synchrony indicates that mechanical activation of the RA leads mechanical activation of the RV, and classifying the tachyarrhythmia episode as VT when the measure of synchrony indicates that the mechanical activation of the RA lags the mechanical activation of the RV.

Example 15 can include or use, or can optionally be combined with the subject matter of one or any combination of Examples 11 through 14 to include or use, calculating a baseline value for the measure of synchrony of mechanical activations. Selecting a device-based therapy can include scheduling a delivery of a device-based therapy at least in part using information about the detected tachyarrhythmia, detecting a change in the measure of synchrony of mechanical activations from the calculated baseline value, and changing at least one of a type of the device-based therapy or the scheduling of the delivery of the device based therapy at least in part using information about the detected change in the measure of synchrony of mechanical activations.

Example 16 can include or use, or can optionally be combined with the subject matter of one or any combination of Examples 11 through 15 to include or use, generating an indication of the heart chamber in which the episode of tachyarrhythmia originated at least in part using information about the measure of synchrony of mechanical activations. The device-based therapy can be selected at least in part using information about the indicated heart chamber of tachyarrhythmia origin.

Example 17 can include or use, or can optionally be combined with the subject matter of one or any combination of Examples 11 through 16 to include or use, a first sensor signal that can include an intracardiac impedance signal sensed for the first heart chamber and a second sensor signal that can include an intracardiac impedance signal sensed for the second heart chamber.

Example 18 can include or use, or can optionally be combined with the subject matter of one or any combination of Examples 11 through 17 to include or use, a first sensor signal that can include an intracardiac pressure signal sensed for the first heart chamber and the second sensor signal that can include an intracardiac pressure signal sensed for the second heart chamber.

Example 19 can include or use, or can optionally be combined with the subject matter of one or any combination of Examples 11 through 18 to include or use, a measure of synchrony of mechanical activations that can include at least one of: (1) a measure of a time delay between onset of the mechanical activation of the first heart chamber and onset of the mechanical activation of the second heart chamber, (2) a measure of a time delay between a time of peak amplitude of the first sensor signal and a time of peak amplitude of the second sensor signal, or (3) a measure of phase shift between the first sensor signal and the second sensor signal, wherein the first and second sensor signals can be frequency domain signals.

Example 20 can include or use or can optionally be combined with the subject matter of one or any combination of Examples 11 through 19 to include or use, determining heart rate of the subject. The measure of synchrony of mechanical activations can include or use at least one of: a measure of a time delay between an onset of a mechanical activation of the first heart chamber and an onset of a mechanical activation of the second heart chamber (which can be normalized, such as with respect to the determined heart rate), and a measure of a delay between a time of peak amplitude of the first sensor signal and a time of peak amplitude of the second sensor signal (which can be normalized, such as with respect to the determined heart rate).

Example 21 can include, or can optionally be combined with any portion or combination of portions of any one or more of Examples 1-20 to include, subject matter that can include means for performing any one or more of the functions of Examples 1-20, or a machine readable medium including instructions that, when performed by a machine, cause the machine to perform any one or more of the functions of Examples 1-20.

Each of these non-limiting examples can stand on its own, or can be combined in various permutations or combinations with one or more of the other examples.

An ambulatory medical device may include one or more of the features, structures, methods, or combinations thereof described herein. For example, a cardiac monitor or a cardiac stimulator may be implemented to include one or more of the advantageous features or processes described herein. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods.

The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An apparatus comprising:
   an implantable sensor circuit configured to generate a first sensor signal, different from an intrinsic electrical cardiac signal, representative of mechanical activation of a first chamber of a heart of a subject and a second sensor signal, also different from an intrinsic electrical cardiac signal, representative of mechanical activation of a second chamber of the heart;
   a chamber synchrony measurement circuit configured to generate a measure of synchrony of the mechanical activations of the first heart chamber and the second heart chamber using the first and second sensor signals;
   a tachyarrhythmia detector circuit configured to detect tachyarrhythmia using a sensed intrinsic electrical cardiac signal; and
   a control circuit communicatively coupled to implantable sensor circuit, the chamber synchrony measurement circuit, and the tachyarrhythmia detector circuit, wherein the control circuit is configured to:
      receive an indication of an episode of tachyarrhythmia detected using the sensed intrinsic electrical cardiac signal;
      classify the episode as supraventricular tachyarrhythmia (SVT) or ventricular tachyarrhythmia (VT) according to the measure of synchrony of the mechanical activations in response to the tachyarrhythmia detection; and
      initiate or adjust a device-based therapy at least in part using the tachyarrhythmia classification.

2. The apparatus of claim 1, wherein the control circuit is configured to:
   classify the tachyarrhythmia episode as SVT or VT according to a sequence of mechanical activation of the first and second heart chambers; and
   initiate, select, or adjust the device-based therapy at least in part using the indicated sequence of mechanical activation.

3. The apparatus of claim 2,
   wherein the implantable sensor circuit is configured to provide a signal representative of mechanical activation of the left ventricle (LV) of the heart as the first sensor signal and provide a signal representative of mechanical activation of the right ventricle (RV) of the heart as the second sensor signal, and
   wherein the control circuit is configured to:
      classify the detected tachyarrhythmia episode as SVT when the measure of synchrony indicates that mechanical activation of the LV lags mechanical activation of the RV, and
      classify the detected tachyarrhythmia episode as VT when the measure of synchrony indicates that the mechanical activation of the LV leads the mechanical activation of the RV.

4. The apparatus of claim 2,
   wherein the implantable sensor circuit is configured to provide a signal representative of mechanical activation of the right atrium (RA) of the heart as the first sensor signal and provide a signal representative of mechanical activation of the RV of the heart as the second sensor signal, and wherein the control circuit is configured to:
classify the tachyarrhythmia episode as SVT when the measure of synchrony indicates that mechanical activation of the RA leads mechanical activation of the RV; and
classify the tachyarrhythmia episode as VT when the measure of synchrony indicates that the mechanical activation of the RA lags the mechanical activation of the RV.

5. The apparatus of claim 1,
wherein the chamber synchrony measurement circuit is configured to calculate a baseline value for the measure of synchrony of mechanical activations, and
wherein the control circuit is configured to:
schedule a delivery of a device-based therapy according to the detected tachyarrhythmia;
detect a change in the measure of synchrony of mechanical activations from the calculated baseline value; and
change at least one of a type of device-based therapy or a time the delivery of the device based therapy is scheduled according to the detected change in the measure of synchrony of mechanical activations.

6. The apparatus of claim 1, wherein the control circuit is configured to:
determine in which heart chamber the episode of tachyarrhythmia originated according to the measure of synchrony of mechanical activations; and
initiate, select, or adjust the device-based therapy at least in part using the determined heart chamber of tachyarrhythmia origin.

7. The apparatus of claim 1, wherein the implantable sensor circuit includes an intracardiac impedance sensing circuit configured to provide a first intracardiac impedance signal sensed for the first heart chamber as the first sensor signal and provide a second intracardiac impedance signal sensed for the second heart chamber as the second sensor signal.

8. The apparatus of claim 1, wherein the implantable sensor circuit includes an intracardiac pressure sensing circuit configured to provide a first intracardiac pressure signal sensed for the first heart chamber as the first sensor signal and provide a second intracardiac pressure signal sensed for the second heart chamber as the second sensor signal.

9. The apparatus of claim 1, wherein the chamber synchrony measurement circuit is configured to:
measure at least one of:
a time delay between onset of the mechanical activation of the first heart chamber and onset of the mechanical activation of the second heart chamber;
a delay between a time of peak amplitude of the first sensor signal and a time of peak amplitude of the second sensor signal; and
phase shift between the first sensor signal and the second sensor signal, wherein the first and second sensor signals are frequency domain signals; and
provide the least one of the measured time delay between onsets, the measured delay between times of peak amplitude, and the measured phase shift as the measure of synchrony of the mechanical activations.

10. The apparatus of claim 1, including:
a cardiac depolarization detector circuit, and
wherein the chamber synchrony measurement circuit is configured to:
determine a heart rate of the subject using detected cardiac depolarization;
measure at least one of:
a measure of a time delay between onset of the mechanical activation of the first heart chamber and onset of the mechanical activation of the second heart chamber normalized with respect to a determined heart rate; and
a measure of a delay between a time of peak amplitude of the first sensor signal and a time of peak amplitude of the second sensor signal normalized with respect to the determined heart rate; and
provide the least one of the normalized measured time delay between onsets or the normalized measured delay between times of peak amplitude as the measure of synchrony of the mechanical activations.

11. A method of operating an implantable medical device comprising:
sensing a first sensor signal, different from an intrinsic electrical cardiac signal, representative of mechanical activation of a first chamber of a heart of a subject using the implantable medical device;
sensing a second sensor signal, also different from an intrinsic electrical cardiac signal, representative of mechanical activation of a second chamber of the heart;
generating a measure of synchrony of the mechanical activations of the first heart chamber and the second heart chamber using the first and second sensor signals;
detecting an episode of tachyarrhythmia using a sensed intrinsic electrical cardiac signal;
classifying the episode as supraventricular tachyarrhythmia (SVT) or ventricular tachyarrhythmia (VT) according to the measure of synchrony of the mechanical activations in response to the tachyarrhythmia detection; and
initiating or adjusting a device-based therapy to be delivered at least in part using the tachyarrhythmia classification.

12. The method of claim 11, including:
classifying the detected tachyarrhythmia episode as SVT or VT according to a sequence of mechanical activation of the first and second heart chambers, and wherein the device-based therapy is selected at least in part using the indicated sequence of mechanical activation.

13. The method of claim 12,
wherein the first sensor signal is representative of mechanical activation of the LV of the heart and the second sensor signal is representative of mechanical activation of the RV of the heart, and
wherein classifying the tachyarrhythmia episode as SVT or VT includes classifying the tachyarrhythmia episode as SVT when the measure of synchrony indicates that mechanical activation of the LV lags mechanical activation of the RV, and classifying the tachyarrhythmia episode as VT when the measure of synchrony indicates that the mechanical activation of the LV leads the mechanical activation of the RV.

14. The method of claim 12,
wherein the first sensor signal is representative of mechanical activation of the RA of the heart and the second sensor signal is representative of mechanical activation of the RV, and
wherein classifying the tachyarrhythmia episode as SVT or VT includes classifying the tachyarrhythmia episode as SVT when the measure of synchrony indicates that mechanical activation of the RA leads mechanical activation of the RV, and classifying the tachyarrhythmia episode as VT when the measure of synchrony indicates that the mechanical activation of the RA lags the mechanical activation of the RV.

15. The method of claim 11, including:
calculating a baseline value for the measure of synchrony of mechanical activations, and
wherein selecting a device-based therapy includes:
- scheduling a delivery of a device-based therapy according to the detected tachyarrhythmia;
- detecting a change in the measure of synchrony of mechanical activations from the calculated baseline value; and
- changing at least one of a type of the device-based therapy or the scheduling of the delivery of the device based therapy at least in part using the detected change in the measure of synchrony of mechanical activations.

16. The method of claim 11, including:
generating an indication of the heart chamber in which the episode of tachyarrhythmia originated according to the measure of synchrony of mechanical activations, and
wherein the device-based therapy is selected at least in part using the indicated heart chamber of tachyarrhythmia origin.

17. The method of claim 11, wherein the first sensor signal includes an intracardiac impedance signal sensed for the first heart chamber and the second sensor signal includes an intracardiac impedance signal sensed for the second heart chamber.

18. The method of claim 11, wherein the first sensor signal includes an intracardiac pressure signal sensed for the first heart chamber and the second sensor signal includes an intracardiac pressure signal sensed for the second heart chamber.

19. The method of claim 11, wherein the measure of synchrony of mechanical activations includes at least one of:
- a measure of a time delay between onset of the mechanical activation of the first heart chamber and onset of the mechanical activation of the second heart chamber;
- a measure of a delay between a time of peak amplitude of the first sensor signal and a time of peak amplitude of the second sensor signal; and
- a measure of phase shift between the first sensor signal and the second sensor signal, wherein the first and second sensor signals are frequency domain signals.

20. The method of claim 11, including:
determining heart rate of the subject, and
wherein the measure of synchrony of mechanical activations includes at least one of:
- a measure of a time delay between onset of the mechanical activation of the first heart chamber and onset of the mechanical activation of the second heart chamber normalized with respect to the determined heart rate; and
- a measure of a delay between a time of peak amplitude of the first sensor signal and a time of peak amplitude of the second sensor signal normalized with respect to the determined heart rate.

\* \* \* \* \*